United States Patent [19]

Oudenes

[11] Patent Number: 4,808,741

[45] Date of Patent: Feb. 28, 1989

[54] PROCESS FOR PREPARING CARBOXYALKYL DIPEPTIDES

[75] Inventor: Jan Oudenes, Thornhill, Canada

[73] Assignee: Torcan Chemical Ltd., Aurora, Canada

[21] Appl. No.: 947,236

[22] Filed: Dec. 29, 1986

[30] Foreign Application Priority Data

Dec. 30, 1986 [ES] Spain .................................. 550.527

[51] Int. Cl.$^4$ ............................................. C07F 7/10
[52] U.S. Cl. ................................................... 556/418
[58] Field of Search ......................................... 556/418

[56] References Cited

U.S. PATENT DOCUMENTS 2,789,122 4/1957 Cason et al. ........................ 556/418
3,517,041 6/1970 Schaar et al. ...................... 556/418
3,864,373 2/1975 Seiler et al. ..................... 556/418 X Primary Examiner—Paul F. Shaver
Attorney, Agent, or Firm—Roylance, Abrams, Berdo & Goodman

[57] ABSTRACT

Pharmaceutically active carboxyalkyl dipeptides such as enalapril, lisinopril and the like, are prepared from a starting amino acid such as L-alanine, by protecting the acid function of the amino acid with an alkyl silyl protecting group, while it is reacted with an α-halo ester, at its amino function. Subsequently, the silyl protectant is removed, and the acid group is reacted with the amino function of an appropriate amino acid such as L-proline, to form the dipeptide product.

8 Claims, No Drawings

PROCESS FOR PREPARING CARBOXYALKYL DIPEPTIDES

FIELD OF THE INVENTION

This invention relates to chemical synthesis of pharmaceutically active chemical compounds, and intermediates of use therein. More specifically, it relates to processes for making dipeptide derivatives and intermediates useful therein.

BACKGROUND AND PRIOR ART

U.S. Pat. No. 4,374,829 Harris et al, issued Feb. 22, 1983, and U.S. Pat. No. 4,472,380 Harris et al issued Sept. 18, 1984, both describe certain carboxyalkyl dipeptide derivatives useful as hypertensives, and processes for their preparation. Among the preferred compounds in these patents is 1-[N-[(S)]-1-carboxy-3-phenylpropyl]-L-alanyl]-L-proline 1'-ethyl ester, referred to herein as enalapril, and having the chemical formula:

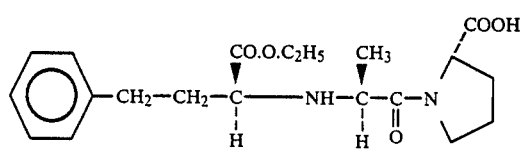

and N-1-[1(S)-carboxy-3-phenylpropyl]-L-lysyl-L-proline, referred to herein as lisinopril, and having the chemical formula:

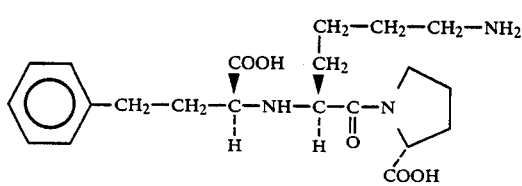

In the process specifically described and exemplified in the aforementioned patents [Examples 26, 43 and 57), a diaminoacid e.g. L-alanyl-L-proline or L-lysyl-L-proline, with t-butoxy-carbonyl protection of the acid function thereof, is condensed with 2-oxo-4-phenylbutyric acid, in the presence of sodium cyanoborohydride. General reference is made to an alternative process in which, in a final stage, appropriately protected proline is reacted with an esterified phenalkylamino acid.

It is known to prepare dipeptide derivatives by reaction of N-(1-carboethoxy-3-phenylpropyl)-α-aminopropionic acid, of formula:

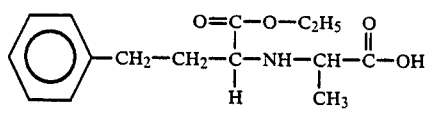

with appropriate amino acids, by reaction of the acid moiety thereof with the amino group of the amino acid. When a proline moiety is used as the amino acid, enalapril can be formed. When other amino acids are chosen, a variety of ACE-inhibiting compounds can be formed. Thus, the compound N-(1-carboethoxy-3-phenylpropyl)-α-aminopropionic acid, (also known as N-(1-ethoxycarbonyl-3-phenylpropyl)-L-alanine), and the similar compounds corresponding to the general formula:

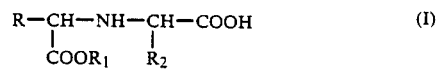

where R represents phenalkyl, $R_1$ represents lower alkyl, phenyl or benzyl, and $R_2$ represents lower alkyl, lower alkyl amino or N-substituted lower alkyl amino, represent valuable synthetic intermediates in the preparation of dipeptide derivative compounds.

SUMMARY OF THE INVENTION

It is an object of the present invention to provide a novel process of preparing amino acid derivatives of general formula I given above.

It is a further object of the invention to provide a novel process of preparing enalapril, lisinopril and similar dipeptide derivatives using compounds of formula I, and to provide novel intermediate compounds used in such preparations.

The present invention involves the synthesis of novel, alkylsilyl protected aminoacids of the general formula II

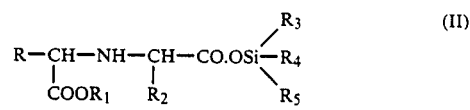

which upon hydrolysis form the substituted amino acid compounds of the general formula I:

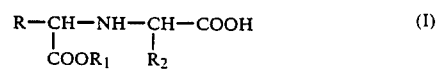

the group R representing phenalkyl, the group $R_1$ representing a hydrolyzable hydrocarbon group such as lower alkyl, phenyl or benzyl, the groups $R_1$, $R_3$, $R_4$ and $R_5$ each representing independently selected lower alkyl groups, and the group $R_2$ representing a lower alkyl or lower alkylamino or N-protected lower alkyl amino group. Amino acid derivative I is readily reacted with another amino acid e.g. proline to form the desired carboxyalkyl dipeptide base product, which can, if desired, be converted to a suitable salt e.g. the maleate salt.

DESCRIPTION OF THE PREFERRED EMBODIMENTS

In the case of enalapril preparation according to the invention, the alkyl silyl intermediate compound II has phenethyl for R, ethyl for $R_1$, and methyl for $R_2$. This compound, of general formula IIa:

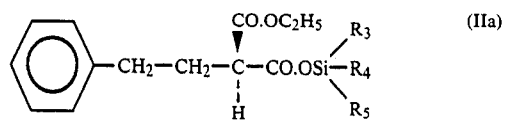

where $R_3$, $R_4$ and $R_5$ are, for example, methyls, may be prepared from the very cheap and abundant starting material L-alanine, in two simple, high yield chemical process steps. Firstly, the L-alanine is silylated e.g. by reaction with hexamethyldisilazane (HMDS):

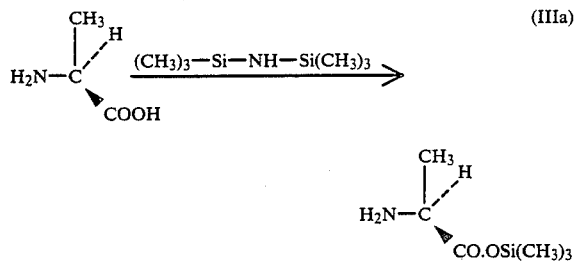

Such silylation can be conducted under standard conditions for reacting HMDS. Details of such standard conditions are well-known to those skilled in the art, and are available from standard texts, such as "Silylation of Organic Compounds" by A. E. Pierce, published by Pierce Chemical Company, Rockford, Ill., especially chapter 8 thereof.

This reaction is best performed under conditions of carefully controlled stoichiometry of reagents, to maximize the formation of the acid silylated product IIIa, and minimize the formation of the di-silylated by-product of formula:

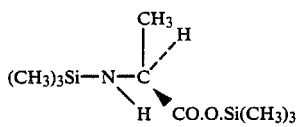

By proper control, formation of this by-product can be effectively eliminated so that the reaction scheme may proceed to the next stage without tedious recovery, separation and purification procedures.

The second chemical process step is the reaction of silyl-protected amino-acid IIIa with ethyl(1-phenyl-3-halo)butyrate, thus:

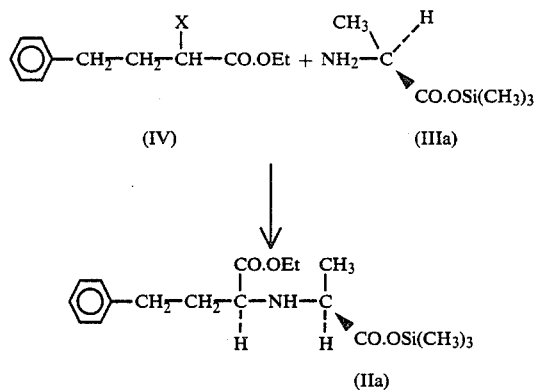

where X represents a halogen such as chlorine, bromine or iodine. This reaction suitably takes place in a basic organic solvent such as triethylamine. It is preferred to use, as the reagent to react with the silylated L-alanine, ethyl (γ-phenyl-α-bromo)-n-butyrate, this reagent being readily commercially available and suitable reactive under moderate conditions to give compound IIa and analogues thereof in high yield.

These first and second steps can, if desired, be performed substantially simultaneously, with the silylating reagent and the ethyl(1-phenyl-3-halo)butyrate present in the same reaction vessel along with the starting aminoacid. The silylation step actually proceeds first, even under such conditions.

Compounds of general structure II are novel, and constitute a significant feature of the present invention. The use of alkylsilyl group for protectant purposes, in place of the normal t-O-butyl protectant, provides significant and unexpected practical advantages. Firstly, it is much more chemically satisfactory in use. The protection with t-O-butyl requires initially the reaction of the amino-acid starting material, e.g. L-alanine, with tert.butyl alcohol (trimethyl carbinol) which is a lengthy and tedious chemical procedure. Secondly, the reaction with t-butyl alcohol leads to the formation of significant amounts of side products, the formation of which cannot be suppressed by simple adjustment of reaction conditions, so that extraction and purification of the desired t-O-butyl protected derivative is necessary, adding tedious and time consuming process steps to the procedure. Thirdly, the subsequent removal of the t-O-butyl protecting group ready for subsequent reaction with amino acid is a further tedious process step, involving acid reflux, and involving side reactions, so that the product thereof must be carefully isolated and purified, a further process step in the overall procedure.

In contrast, according to the present invention, the alkylsilyl protecting group is readily and selectively incorporated on the acid group of the starting amino acid, by simple adjustments of the relative reagent amounts. Isolation and purification of the silyl protected L-alanine (formula III) is not in fact necessary. Following simple removal of excess salts, and perhaps washing of the product, the procedure may proceed directly, in the same reaction vessel, to preparation of compound IIa.

On account of economy and readily availability of reagents, it is preferred to use methylsilyl as protectant, by reaction with hexamethyl-disilazane, HMDS. However, the process of the present invention is not restricted thereto, other lower alkyl groups being substitutable for the methyl groups in the alkylsilyl protectant.

Further, it is not necessary to recover the compound IIa before proceeding with the next stage of the procedure. The silylated intermediate IIa is next hydrolysed with water or mild alkali, to remove the alkyl-silyl protectant and form intermediate acid I:

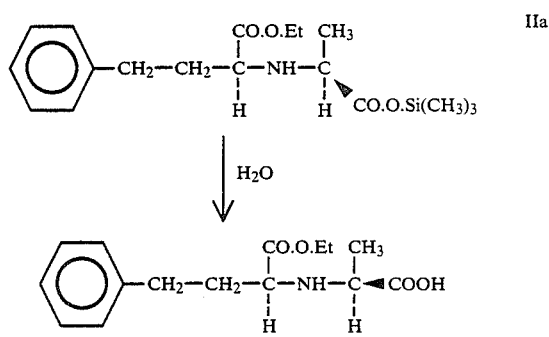

The reaction takes place under mild reaction conditions to give substantially quantitative yields of compound I(a). It is suitably isolated as its hydrochloride salt, and diastereoisomers are separated therefrom, according to known literature procedures.

A particularly preferred procedure for separation of stereoisomers involves the preparation of the hydrochloride addition salts, and the utilization of their differential solubilities in isopropanol.

Then the compound of formula I or its salt may be reacted with an appropriately chosen amino acid, to prepare the dipeptide derivative of pharmaceutical activity. When it is desired to prepared lisinopril or enalapril, the amino acid is proline. Preferably, the proline is protected at its acid function, e.g. by an ester group such as a benzyl ester or lower alkyl ester, to minimize side reactions, thus:

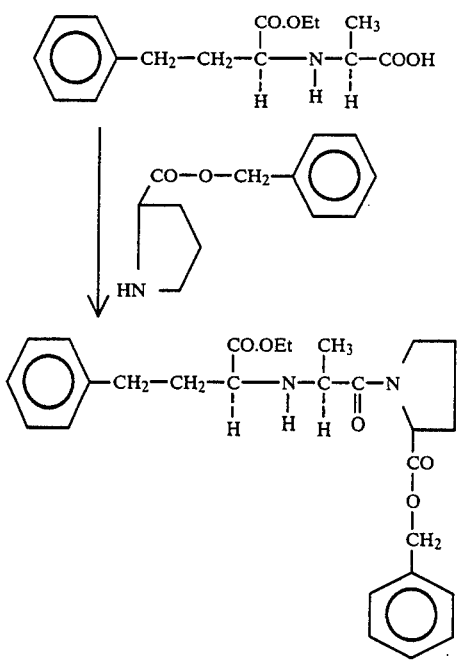

Suitably this reaction takes place in the presence of a basic organic solvent such as triethylamine and/or dicyclohexylcarbodiimide, in the known manner. Then the proline group is deprotected, e.g. by use of hydrogen over a palladium-carbon catalyst, to remove the benzyl protecting group, and thus produce the final compound enalapril. When it is desired to prepare other dipeptide derivatives containing other moieties than the proline moiety, then a protected amino acid other than proline is chosen. Preparation of lisinopril proceeds in an analogous manner to that of enalapril, except that L-lysine is used, in silyl protected form, instead of L-alanine. Also, in the case of lisinopril preparation according to the invention, the alkylsilyl intermediate compound II similarly has phenethyl for R. The group $R_1$ however, can be any appropriately chosen, subsequently removable lower alkyl group (eg. methyl), phenyl or benzyl group, since the group is subsequently hydrolyzed to give the free acid. Also the group $R_2$ is either Δ-amino-n-butyl or preferably N-protected Δ-amino-n-butyl, the protecting group being readily hydrolyzable as a final stage to give the free amine in lisinopril.

SPECIFIC DESCRIPTION OF THE MOST PREFERRED EMBODIMENTS

The process and products of the present invention are further illustrated by the following specific examples:

EXAMPLE 1

N-(1-R,S-Ethoxycarbonyl-3-phenylpropyl)-L-alanine

A mixture of 21.7 g of L-alanine, 35.6 g of hexamethyldisilazane, 27.9 g of triethylamine and 375 mL of acetonitrile is refluxed for three hours. Then 74.9 g of ethyl 2-bromo-4-phenylbutanoate is added and the resulting solution is refluxed for 24 hours. The volatiles are removed by distillation and the residue subsequently cooled and added to a vigorously stirred mixture of 75 mL of water and 375 mL of dichloromethane. The organic layer is separated, dried over anhydrous sodium sulfate and concentrated in vacuo; the residue is then added to 750 mL of refluxing ethyl acetate. The mixture is filtered, slowly cooled to room temperature and then placed in an ice bath. Filtration and drying in vacuo afforded 48.8 g of N-(1-R,S-ethoxycarbonyl-3-phenylpropyl)-L-alanine.

EXAMPLE 2

N-(1-S-Ethoxycarbonyl-3-phenylpropyl)-L-alanine hydrochloride

A solution of diastereomeric N-(1-R,S-ethoxycarbonyl-3-phenylpropyl)-L-alanine in 400 mL of 1,2-dichloroethane is warmed to 50° C. and saturated with dry gaseous hydrogen chloride. Upon saturation the mixture is cooled to room temperature, filtered and dried in vacuo to give 28.8 g of N-(1-R-ethoxycarbonyl-3-phenylpropyl)-L-alanine hydrochloride.

The filtrate is concentrated in vacuo and the resulting residue is recrystallized from 300 mL of ethyl acetate. The stirred mixture is slowly cooled to room temperature, filtered and dried in vacuo to give 28.8 g of N-(1-S-ethoxycarbonyl-3-phenylpropyl)-L-alanine hydrochloride.

EXAMPLE 3

N-(1-S-Ethoxycarbonyl-3-phenylpropyl)-L-alanine

A mixture of 37.4 of L-alanine, 42.4 g of triethylamine, 100 g of ethyl 2-bromo-4-phenylbutanoate and 100 mL of acetonitrile is heated to reflux and 37.0 of hexamethyl-disilazane is added dropwise. The resulting mixture is refluxed overnight and the volatiles removed by distillation at atmospheric pressure. Toluene (500 mL) is added and the combined mixture is added gradually to 120 mL of 5.1 HCl in isopropanol. The flask is cooled to 0° C. overnight and the less desired diastereomer is filtered off. The filtrate is extracted with 200 mL of water and 20 g of sodium acetate is added to the aqueous extract. The pH is adjusted to pH=5.0 with solid sodium carbonate. The aqueous layer is extracted with methylene chloride (1×200×mL, 1×50 mL). The organic layer is concentrated by distillation at atmospheric pressure followed by addition of 400 mL of ethyl acetate-hexanes (1:1). The mixture is cooled to 0° C. and then filtered to give 39.5 g of the desired product.

EXAMPLE 4

N-[N-(1-S-Ethoxycarbonyl-3-phenylpropyl)-L-alanyl]-L-proline, benzyl ester

A stirred mixture of 5.00 g of N-(1-S-ethoxycarbonyl-3-phenylpropyl)-L-alanine hydrochloride, 3.83 g of proline benzyl ester hydrochloride, 50 mL of dichloromethane and 3.2 g of triethylamine is cooled to −5° C. A solution of 3.26 g of N,N'-dicyclohexylcarbodiimide in 10 mL of dichloromethane is added over 0.5 hour and the resulting reaction mixture stirred for 24 hours at −5° C. Then the mixture is filtered, washed with saturated sodium bicarbonate, dried over anhydrous sodium sulfate and concentrated in vacuo to yield 6.86 g of N-[N-(1-S-ethoxycarbonyl-3-phenylpropyl)-L-alanyl]-L-proline, benzyl ester, i.e. the benzyl ester of enalapril, which can be hydrogenated to produce enalapril (see following Example 5).

EXAMPLE 5

N-[N-(1-S-Ethoxycarbonyl-3-phenylpropyl)-L-alanyl]-L-proline, benzyl ester

A mixture of 43.4 g of L-alanine, 48.4 g of triethylamine, 50.0 g of hexamethyldisilazane and 700 mL of acetonitrile is refluxed under a slow stream of nitrogen for 3 hours. Then 100.0 g of ethyl 2-bromo-4-phenylbutanoate is added and the mixture refluxed for 24 hours. During the final hours of this period acetonitrile is distilled off. Subsequently, the residue is slowly cooled to room temperature, 500 mL of dry toluene is gradually added and the stirred mixture is cooled to 0° C. The mixture is filtered under anhydrous conditions and the crystals are washed with 100 mL of dry toluene to yield, upon drying, 52 g of triethylammonium bromide.

The filtrate is added dropwise to a solution of 120 mL of 5.0N hydrogen chloride in isopropanol which is warmed to 60° C. The stirred mixture is slowly cooled to room temperature and then cooled to 0° C. overnight. The crystals are filtered and washed with a little cold solution of isopropanol in toluene. Upon drying in vacuo, 53 g of white crystalline N-(1-R-ethoxycarbonyl-3-phenylpropyl)-L-alanine hydrochloride is obtained.

The filtrate is added to 200 mL of ice water and the aqueous extract is treated with 20.0 g of sodium acetate. Solid sodium carbonate is added to adjust the pH to 4.5–5.0 and the aqueous phase is extracted once with 200 mL of dichloromethane and once with 100 mL of dichloromethane. The combined organic extracts are treated with celite and anhydrous sodium sulfate and then filtered to yield a clear, tan coloured solution which contains ca. 53 g of N-(1-S-ethoxycarbonyl-3-phenylpropyl)-L-alanine which optionally can be isolated by evaporation to dryness and recrystallization.

The solution containing N-(1-S-ethoxycarbonyl-3-phenylpropyl)-L-alanine is added to a mixture of L-proline benzyl ester hydrochloride, 200 mL of dichloromethane and 18.65 g of triethylamine at −5° C. Then a solution of 38.0 g of N,N′-dicyclohexylcarbodiimide in 100 mL of dichloromethane is added dropwise over a one hour period. The resulting reaction mixture is stirred at −5° C. for 24 hours and then filtered. The filtrate is washed with 100 mL of water, followed by 50 mL of saturated sodium bicarbonate. The organic phase is dried over anhydrous sodium sulfate, filtered and concentrated in vacuo to give 86 g of a clear, amber coloured N-[N-(1-S-ethoxycarbonyl-3-phenylpropyl)-L-alanyl]-L-proline, benzyl ester.

EXAMPLE 6

N-[N-(1-S-Ethoxycarbonyl-3-phenylpropyl)-L-alanyl]-L-proline, maleate

A solution of 10 g of N-[N-(1-S-ethoxycarbonyl-3-phenylpropyl)-L-alanyl]-L-proline benzyl ester is hydrogenated with 1.0 g of 10% palladium on carbon and hydrogen for one hour. The reaction mixture is filtered through celite and concentrated in vacuo to give 8.0 g of N-[N-(1-S-ethoxycarbonyl-3-phenylpropyl)-L-alanyl]-L-proline.

A solution of 8.0 g of N-[N-(1-S-ethoxycarbonyl-3-phenylpropyl)-L-alanyl]-L-proline in 26 mL of acetonitrile is treated with 2.60 g of maleic acid and then heated to reflux. After cooling to 0° C. overnight, the mixture is filtered to give 6.6 g of a white crystalline product. Crystallization from 33 mL of acetonitrile yields 6.0 g of N-[N-(1-S-ethoxycarbonyl-3-phenylpropyl)-L-alanyl]-L-proline, maleate; m.p. 150°–151° C.; $[\alpha]_D^{25} = -42°$ (C, 1% in methanol).

EXAMPLE 7

[$N_\alpha$-(1-R,S-Methoxycarbonyl-3-phenylpropyl)-$N_\epsilon$-(benzyloxycarbonyl)]-L-lysine A mixture of 30.8 g of $N_\epsilon$-(benzyloxycarbonyl)-L-lysine, 25.7 g of methyl 2-bromo-4-phenylbutanoate, 10.1 g of triethylamine, 11.2 g of hexamethyldisilazane and 500 mL of acetontrile is refluxed under a slow stream of nitrogen for several days. The reaction is then quenched with water and the volatiles are removed in vacuo. The residue is extracted with 500 mL of ethyl acetate and formed triethylammonium bromide is removed by filtration. The filtrate is concentrated in vacuo and the residue triturated with ether. The mixture is cooled to 0° C., filtered and dried in vacuo to yield 39.5 g of [$N_\alpha$-(1-R,S-methoxycarbonyl-3-phenylpropyl)-$N_\epsilon$-(benzyloxycarbonyl)]-L-lysine.

EXAMPLE 8

$N_\alpha$-(1-S-Methoxycarbonyl-3-phenylpropyl)-$N_\epsilon$-(benzyloxycarbonyl)-L-lysine A diastereomeric mixture of 90 g of $N_\alpha$-(1-R,S-methoxycarbonyl-3-phenylpropyl)-$N_\epsilon$-(benzyloxycarbonyl)-L-lysine is dissolved in 400 mL of refluxing acetonitrile. The solution is stirred overnight at room temperature and then filtered to give 28.0 g of white product. Recrystallization in acetonitrile affords 21.7 g of $N_\alpha$-(1-S-methoxycarbonyl-3-phenylpropyl)-$N_\epsilon$-(benzyloxycarbonyl)-L-lysine as a pure diastereomer.

EXAMPLE 9

N-[$N_\alpha$-(1-S-Methoxycarbonyl-3-phenylpropyl)-$N_\epsilon$-(benzyloxycarbonyl)-L-lysinyl]-L-proline, methyl ester A mixture of 35 g of $N_\alpha$-(1-S-methoxycarbonyl-3-phenylpropyl)-$N_\epsilon$-(benzyloxycarbonyl)-L-lysine, 12.66 g of L-proline methyl ester hydrochloride, 7.75 g of triethylamine and 350 mL of dichloromethane is cooled to −5° C. and then a solution of N,N-dicyclohexylcarbodiimide in 100 mL of dichloromethane is added over a one hour period. The resulting mixture is stirred at −5° C. for 24 hours, filtered, washed once with 100 mL of water and then with 50 mL of saturated sodium carbonate. The organic phase is separated, dried with anhydrous sodium sulfate, filtered and concentrated in vacuo to yield 44.5 g of N-[$N_\alpha$-(1-S-methoxycarbonyl-3-phenylpropyl)-$N_\epsilon$-(benzyloxycarbonyl)-L-lysinyl]-L-proline, methyl ester as a colourless oil.

EXAMPLE 10

N-[$N_\alpha$-(1-S-Carboxy-3-phenylpropyl)-L-lysyl]-L-proline

A solution of 26.9 g of N-[$N_\alpha$-(1-S-methoxycarbonyl-3-phenylpropyl)-$N_\epsilon$-(benzyloxycarbonyl)-L-lysinyl]-L-proline, methyl ester in 450 mL of methanol is hydrogenated with 2.7 g of 10% palladium on carbon and hydrogen for one hour. The mixture is filtered through celite and concentrated in vacuo to give 20.88 g of N-[N$_\alpha$-(1-S-methoxycarbonyl-3-phenylpropyl)-L-lysinyl]-L-proline, methyl ester, as a clear, colourless oil.

This product is dissolved in 900 mL of distilled water containing 4.60 g of sodium hydroxide. The solution is then filtered and treated once with 200 g of Dowex 50 X4-400 cationic exchange resin and once with 20 g of the resin. The filtered resin is then eluted with a 20:1 mixture of pyridine and water. The eluent is lyophilized to give 15.6 g of the desired material as a white solid. Recrystallization from methanol and ethyl acetate affords 9.6 g of N-[N$_\alpha$-(1-S-carboxy-3-phenylpropyl)-L-lysyl]-L-proline (lisinopril); m.p. 166°–169° C.; $[\alpha]_D^{25} = -36.1°$ (C, 10% in water).

I claim:

1. A process of preparing silylated organic compounds of general formula:

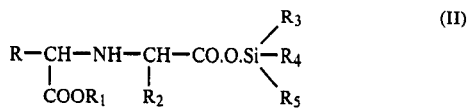

said compounds of formula (II) being readily hydrolyzable to the corresponding substituted amino acid compound ready for reaction with another amino acid compound to form a dipeptide derivative, in which R represents phenalkyl, R$_1$ represents lower alkyl, phenyl or benzyl, R$_2$ represents lower alkyl, lower alkylamino or N-substituted lower alkylamino, and R$_3$, R$_4$ and R$_5$ are independently selected lower alkyl groups, which comprises reacting a silylated amino-acid of the general formula:

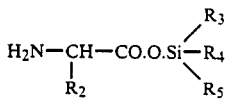

in which R$_2$, R$_3$, R$_4$ and R$_5$ have the meanings given above, with a phenalkyl ester of the general formula:

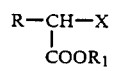

in which R and R$_1$ have the meanings given above, and X is chlorine, bromine or iodine.

2. The process of claim 1 wherein R$_2$ is selected from methyl and N-substituted butylamino.

3. The process of claim 2 wherein R is phenethyl.

4. The process of claim 3 wherein R$_1$ is ethyl.

5. The process of claim 4 wherein each of R$_3$, R$_4$ and R$_5$ is methyl.

6. The process of claim 5 wherein the silylated amino-acid is prepared by reacting an amino-acid of formula:

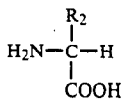

with hexamethyldisilazane.

7. The process of claim 6 which comprises reacting said amino-acid and hexamethyldisilazane to form said silylated amino-acid, and reacting the silylated amino-acid so formed with the phenalkyl ester to form the silylated organic compound, in the same reaction medium and reaction vessel substantially simultaneously as a single process step, without intermediate recovery or isolation of said silylated amino-acid.

8. The process of claim 6 wherein the amino acid and the hexamethyldisilazane are reacted together in substantially stoichiometric quantities appropriate for monosilylation of the amino acid.

* * * * *